US011224452B2

(12) United States Patent
Lu et al.

(10) Patent No.: US 11,224,452 B2
(45) Date of Patent: Jan. 18, 2022

(54) MEDICAL ASSISTIVE DEVICE FOR QUICK POSITIONING OF REDUCTION FORCEPS

(71) Applicant: Hsien-Tsung Lu, Taipei (TW)

(72) Inventors: Hsien-Tsung Lu, Taipei (TW); Michael Lu, Taipei (TW); Brian Lu, Taipei (TW); Rina Lu, Taipei (TW)

(*) Notice: Subject to any disclaimer, the term of this patent is extended or adjusted under 35 U.S.C. 154(b) by 197 days.

(21) Appl. No.: 16/655,256

(22) Filed: Oct. 17, 2019

(65) Prior Publication Data

US 2021/0077137 A1 Mar. 18, 2021

(30) Foreign Application Priority Data

Sep. 12, 2019 (TW) ................................ 108133062

(51) Int. Cl.
*A61B 17/00* (2006.01)
*A61B 17/29* (2006.01)
*A61B 17/88* (2006.01)
*A61B 17/56* (2006.01)

(52) U.S. Cl.
CPC .......... *A61B 17/29* (2013.01); *A61B 17/8866* (2013.01); *A61B 2017/564* (2013.01)

(58) Field of Classification Search
CPC ................ A61B 17/29; A61B 17/8866; A61B 2017/564
See application file for complete search history.

(56) References Cited

U.S. PATENT DOCUMENTS 7,959,635 B1 *  6/2011  Bonutti ............. A61B 17/0401
                                                    606/82
2019/0247050 A1 *  8/2019  Goldsmith ....... A61B 17/00491

* cited by examiner

*Primary Examiner* — Steven O Douglas

(57) ABSTRACT

A medical assistive device for quick positioning which can be combined with surgical reduction forceps rapidly, free from angle limitation, operated more conveniently. It comprises a base, the top surface thereof can hold the patient's wrist region; a socket holder located under the bottom surface of the base, provided with a round cavity-like hole slot; multiple support columns vertically located on the bottom surface of the base, surrounding the socket holder, forming connected passages under the base; a universal joint, embedded in the hole slot of socket holder, flexibly diverted. Thereby, the lower forceps body of surgical reduction forceps can reach the lower part of socket holder at any angle under the base, so that the lower forceps body is combined with the universal joint quickly, the combination is rapid, and the lower forceps body can rotate flexibly.

10 Claims, 12 Drawing Sheets

MEDICAL ASSISTIVE DEVICE FOR QUICK POSITIONING OF REDUCTION FORCEPS

BACKGROUND OF INVENTION

1. Field of the Invention

The present invention relates generally to a medical assistive device, and more particularly to a medical assistive device for quick positioning used with orthopedic reduction forceps.

2. Description of Related Art

The radius is located in the wrist region, where normal persons wear a bracelet or a watch, it is a common position of fracture, especially during an accidental fall, a person sometimes contacts the ground with a hand reflectively, leading to the fracture of radius. The probability of fracture of this region is about ⅒ of human fractures, which is considerable, so it is very important to handle this kind of injury. However, the clinical reduction operation for the fracture of radius sometimes requires two doctors, one is the surgical assistant who must open and fix the surgical incision in the patient's fracture end of radius, so that the doctor can perform the reduction operation for the fracture of radius, the operation room is occupied, and the manpower is wasted.

In order to solve the above problems, the inventor developed a "reduction forceps aid", which has been patented, Taiwan patent M571210, applied on Aug. 31, 2018, the structure thereof is shown in FIG. 9 to FIG. 12. The aid 200 is a square base 8, a clamping part 9 for positioning the reduction forceps is located in the center of bottom surface, there are symmetrical and vertical supporting parts 81 provided on the right and left sides of bottom surface of base 8. The clamping part 9 is located between the left and right supporting parts 81. The clamping part 9 comprises a detent 91 and four fixture blocks 92 equiangularly distributed around the detent 91, there is a spacing 93 between every two fixture blocks 92. When a doctor performs a reduction operation, the spherical part 2013 at the end of lower forceps body 2012 of reduction forceps 20 shall be embedded in the clamping part 9, so that the base 8 is combined with the lower forceps body 2012. Thereby, the patient's wrist region 10 can be fixed to the top surface of the base 8 for the doctor to perform the reduction operation. As the fracture end is well fixed, the clamping is steadier when the doctor uses reduction forceps, no slippage, the operation is easier, and the operating time is shortened, the efficiency is increased. However, the following problems are found in the actual operation which shall be improved.

The supporting parts 81 on the left and right sides of the base 8 in previous project are stopper structures, there is no hollow passage for the lower forceps body 2012 to pass through, only the front and back sides have a passage, directly influencing penetration of the lower forceps body 2012 into the lower part of base 8, so the supporting parts 81 on the left and right sides hinder the lower forceps body 2012, the use is unsmooth, the operating efficiency is influenced.

The clamping part 9 of previous project comprises a detent 91 and four fixture blocks 92. The spherical part 2013 at the end of the lower forceps body 2012 is clamped by the four fixture blocks 92, there is frictional drag during rotation, so that the rotation is unsmooth and the amplitude is too small, the operation technique is influenced, that shall be improved.

Thus, to overcome the problems of the prior art, it would be an advancement in the art to provide an improved structure that can significantly improve the efficacy.

Therefore, the inventor has provided the present invention of practicability after deliberate design and evaluation based on years of experience in the production, development and design of related products.

SUMMARY OF THE INVENTION

The object of the present invention is to provide a medical assistive device for quick positioning of reduction forceps which can be combined with reduction forceps rapidly, so that the reduction forceps operating angle is unrestricted, the patient's hand stability is enhanced, and the operation is more convenient.

The technical scheme is to provide a medical assistive device for quick positioning of reduction forceps, comprising:

a base (1), which is a plate placed under the patient's wrist region, one side thereof is the top surface (11), the opposite side is the bottom surface (12) opposite to the top surface (11), wherein the top surface (11) can be the surface contacting the patient's wrist region;

a socket holder (4), which is a convex base located under the bottom surface (12) of the base (1), normal to the bottom surface (12) can protruding outwards towards the normal axis (C); there is a round cavity-like hole slot (41) in the socket holder (4), the hole slot (41) has a first slot opening (42) opened outwards, the first slot opening (42) is located at the end of socket holder (4), on the same normal axis (C) together with the socket holder (4);

multiple support columns (3), vertically located on the bottom surface (12) of the base (1), surrounding the socket holder (4), longer than the socket holder (4); there are passages (6) for the lower forceps body (2012) of forceps body (201) of reduction forceps (20) to pass through between the support columns (3), and the passages (6) are connected to each other;

a universal joint (5), which is a spherical body, embedded in the hole slot (41) of the socket holder (4), flexibly rotating in the hole slot (41). The universal joint (5) has an embedding slot (51), and the embedding slot (51) has an open second slot opening (52), the hole size thereof is smaller than the first slot opening (42) of socket holder (4); the second slot opening (52) and the first slot opening (42) fit each other, so that the sphere (2013) at the end of lower forceps body (2012) of reduction forceps (20) passes through the second slot opening (52) before it is embedded in the embedding slot (51).

More particularly, the center of the top surface (11) is a concave part (111), on the lowest level, the right and left sides are upwarping parts (112), (112'), on the highest level, the concave part (111) to the right and left upwarping parts (112), (112') rise at a bend angle, so that the top surface (11) becomes a cambered surface.

More particularly, three of the support columns (3) are equiangularly distributed, one of them is exactly located on the bottom surface (12) at one side end of concave part (111) of the top surface (11), which can be the central support column (3'), the three support columns (3) can form three interconnected passages (6).

More particularly, the socket holder (4) is a conical convex base protruding from the lower part of the bottom surface (12) of base and converging outwards; the socket holder (4) and support columns (3) are connected by reinforcing ribs (7); the base (1), support columns (3), socket holder (4) and reinforcing ribs (7) are formed in one.

More particularly, the shape of the base (1) is one of the following shapes, circle, ellipse and polygon.

More particularly, the top surface (11) of the base (1) is provided with an additional carrier part (2) for placing the patient's wrist region; one side of the carrier part (2) is the top surface (21), the opposite side is the bottom surface (22) opposite to the top surface (21), wherein the top surface (21) is the surface contacting the patient's wrist region.

More particularly, there is a convex shaft (23) in the center of the bottom surface (22) of the carrier part (2), there is a pivot hole (13) for the convex shaft (23) in the center of the top surface (11) of the base (1); the convex shaft (23) takes the pivot hole (13) as the axis, so that the carrier part (2) can rotate 360° on the base (1).

More particularly, the carrier part (2) is a soft plastomer; the bottom surface (22) of the carrier part (2) has a concave shallow slot (24) fitted over the upper part of base (1), so that the carrier part (2) can be combined with or disengaged from the base (1) at any time.

More particularly, the carrier part (2) is a soft plastomer, the bottom surface (22) of the carrier part (2) can cover and adhere to the top surface (11) of base (1).

More particularly, the center of top surface (21) of the carrier part is a concave part (211), on the lowest level, the right and left sides are upwarping parts (212), (212'), on the highest level, the concave part (211) to the right and left upwarping parts (212), (212') rise at a bend angle, so that the top surface (21) becomes a cambered surface.

The present invention uses multiple support columns to form connected passages under the base, the lower forceps body of surgical reduction forceps can penetrate the passage at any angle, reaching the lower part of the socket holder rapidly, so that the spherical part at the end of lower forceps body can be combined with a universal joint rapidly, the combination is fast, time saving and more efficient.

The present invention provides a universal joint in the socket holder to reduce the friction with the spherical part of lower forceps body, the base rotation flexibility is enhanced greatly, so that the direction and angle of lower forceps body can be adjusted smoothly, the doctor's operation is more convenient, the operating time is shortened, the efficiency is increased.

By means of the cambered top surface and the upwarping parts on the left and right sides of the base, the patient's wrist region can contact the top surface of base closely, the right and left sides of wrist region are fixed by the upwarping parts to avoid the wrist region slipping from the base.

A carrier part is added to the base of the present invention, when the reduction forceps push the support columns, the base rotates 360° round the normal axis, so that in the reduction operation for the fracture of radius, the doctor can perform rotating operation according to operation requirement at any time, the operation process is easier.

The carrier part of the present invention is a soft plastomer, providing soft, friendly and buffering effects on the wrist region.

DETAILED DESCRIPTION OF THE INVENTION

The detailed description is given below according to the attached figures.

Figure 1:
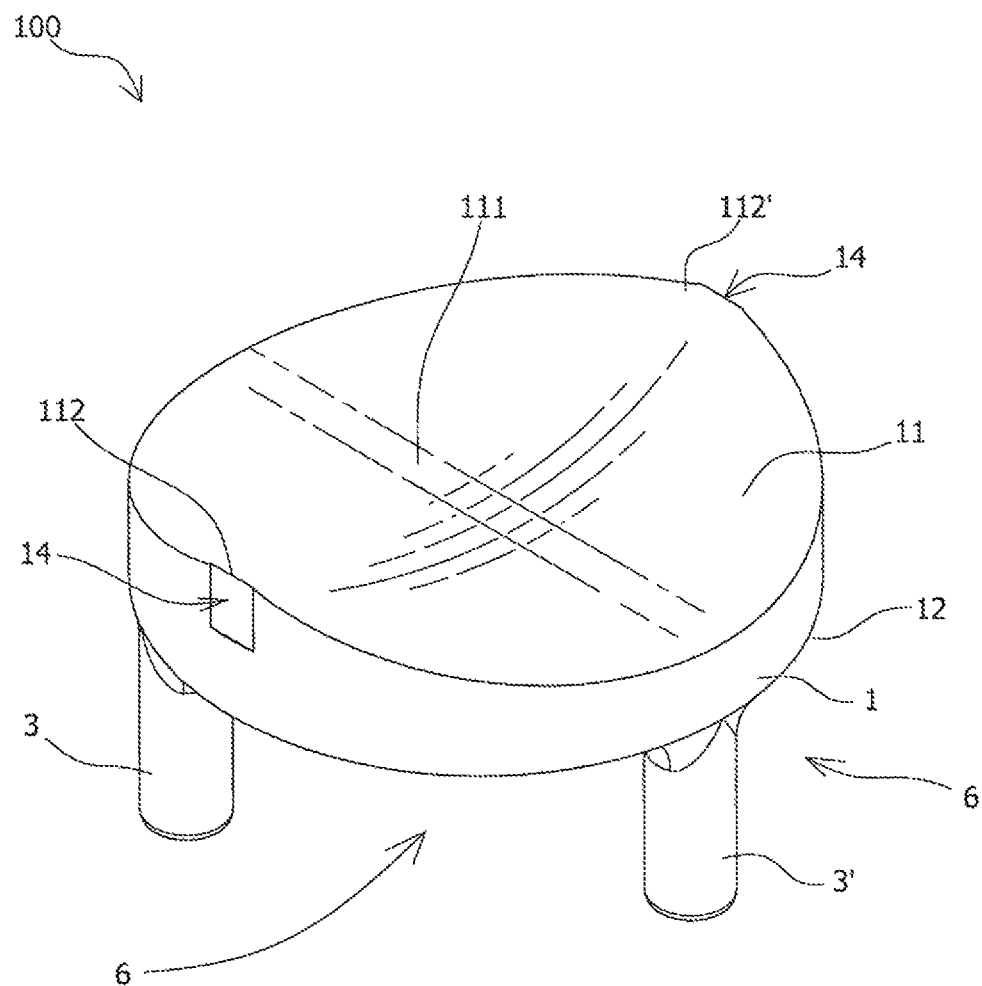
FIG. 1 is a three-dimensional diagram in top view of the first implementation pattern of the present invention.
Figure 2:
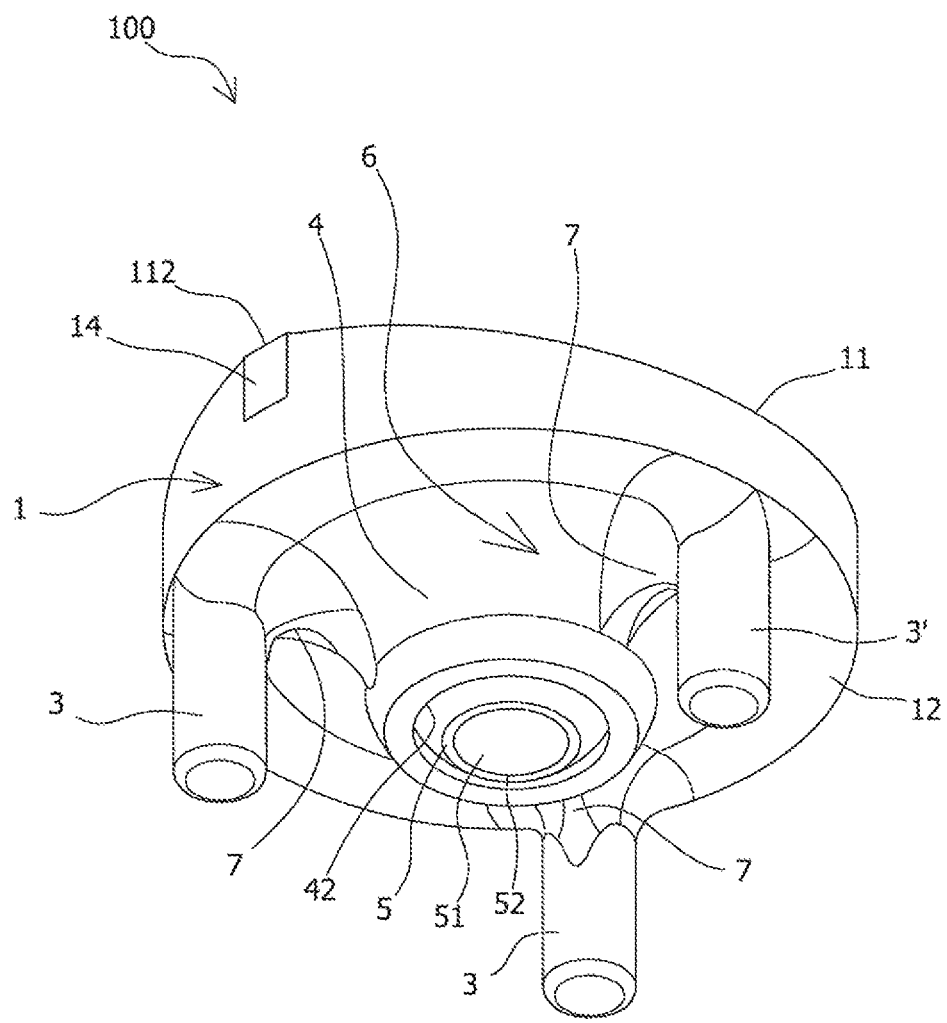
FIG. 2 is a three-dimensional diagram in upward view of the first implementation pattern of the present invention.
Figure 3:
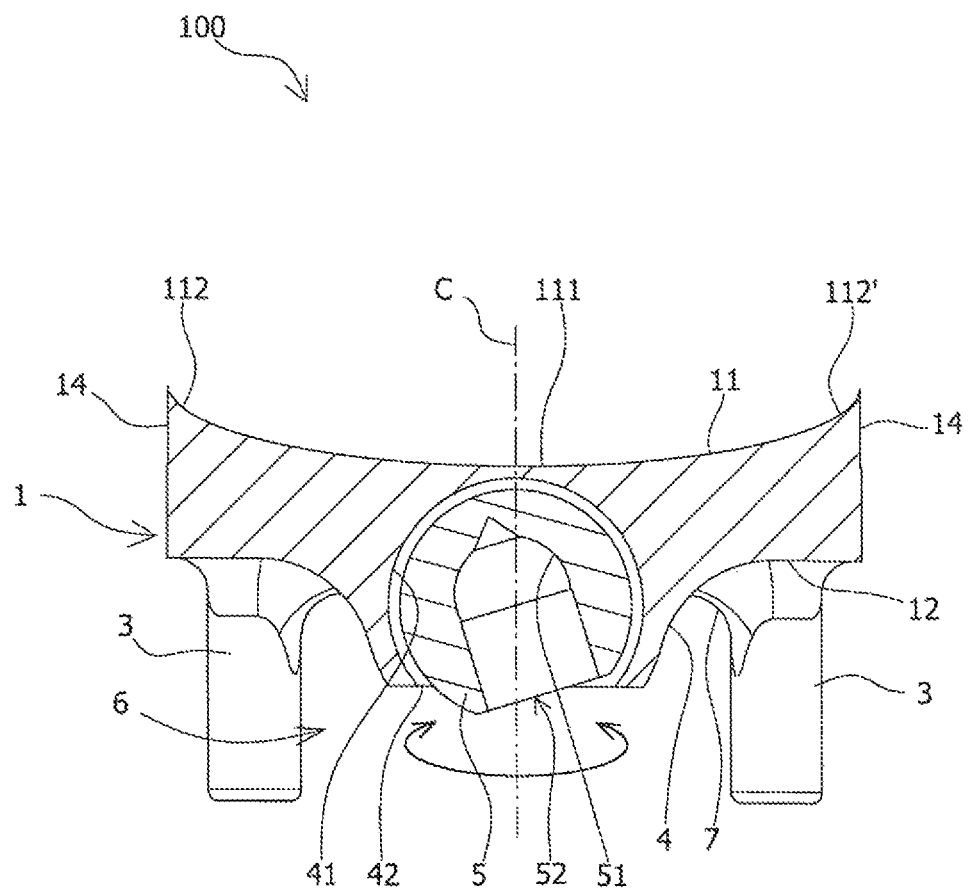
FIG. 3 is a schematic section of the first implementation pattern of the present invention.

FIG. 1 to FIG. 3 disclose the medical assistive device 100 for quick positioning of reduction forceps of the first implementation pattern of the present invention, which comprises a base 1, multiple support columns 3, a socket holder 4 and a universal joint 5; wherein the base 1 is a plate placed under the patient's wrist region, one side thereof is the top surface 11, the opposite side is the bottom surface 12 opposite to the top surface 11. The top surface 11 can be the surface contacting the patient's wrist region. The socket holder 4 is a convex base located under the bottom surface 12 of the base 1, normal to the bottom surface 12 and protruding outwards towards normal axis C. There is a round cavity-like hole slot 41 in the socket holder 4. The hole slot 41 has a first slot opening 42 opened outwards. The first slot opening 42 is located at the end of socket holder 4, on the same normal axis C together with the socket holder 4. The multiple support columns 3 are vertically located on the bottom surface 12 of the base 1, surrounding the socket holder 4, longer than the socket holder 4. There are passages 6 between the support columns 3, and the passages 6 are connected to each other. The universal joint 5 is a spherical body, embedded in the hole slot 41 of the socket holder 4, it can flexibly rotate in the hole slot 41. The universal joint 5 has an embedding slot 51, the embedding slot 51 has an open second slot opening 52, the hole size thereof is smaller than the first slot opening 42 of socket holder 4. The second slot opening 52 and the first slot opening 42 fit each other.

The center of the top surface 11 is a concave part 111, on the lowest level, the right and left sides are upwarping parts 112, 112', on the highest level, the concave part 111 to the right and left upwarping parts 112, 112' rise at a bend angle, so that the top surface 11 becomes a cambered surface. In addition, the concave part 111 is located in the center of top surface 11 as a linear bottom cut, when the patient's wrist region is placed on the base 1, it is used as center line for the doctor to judge matching with naked eye.

There are multiple support columns 3 as mentioned above, there are three columns in this figure, arranged equiangularly round the socket holder 4 as center, so the three support columns 3 under the base 1 form three interconnected passages 6. In addition, one of the three support columns 3 is exactly located on the bottom surface 12 at one side end of the concave part 111, which is called central support column 3'. The central support column 3' can be the base 1 placement baseline after corresponding to the concave part 111, for the doctor to check whether the wrist region is placed on the base 1 correctly or not.

Secondly, the socket holder 4 is a conical convex base protruding from the lower part of bottom surface 12 of base and converging outwards. The end of the conical convex base is a plane, the first slot opening 42 is located in the plane. The socket holder 4 is connected to the support columns 3 by reinforcing ribs 7. The base 1, support columns 3, socket holder 4 and reinforcing ribs 7 are formed in one, forming a consolidated structure. The socket holder 4 is conical, and it can be cylindrical.

The square base 1 can be replaced by one of such shapes as circle, ellipse and polygon. The base shapes are more convenient for the doctor to operate. In addition, the outer walls of the upwarping parts 112, 112' on the left and right sides of base 1 are partially cut off to form cutting faces 14, so as to avoid sharp edges forming at the upper ends of upwarping parts 112, 112'. In another way, the upper end edges of the upwarping parts 112, 112' are ground into round lips to overcome sharp edges.

Figure 4:
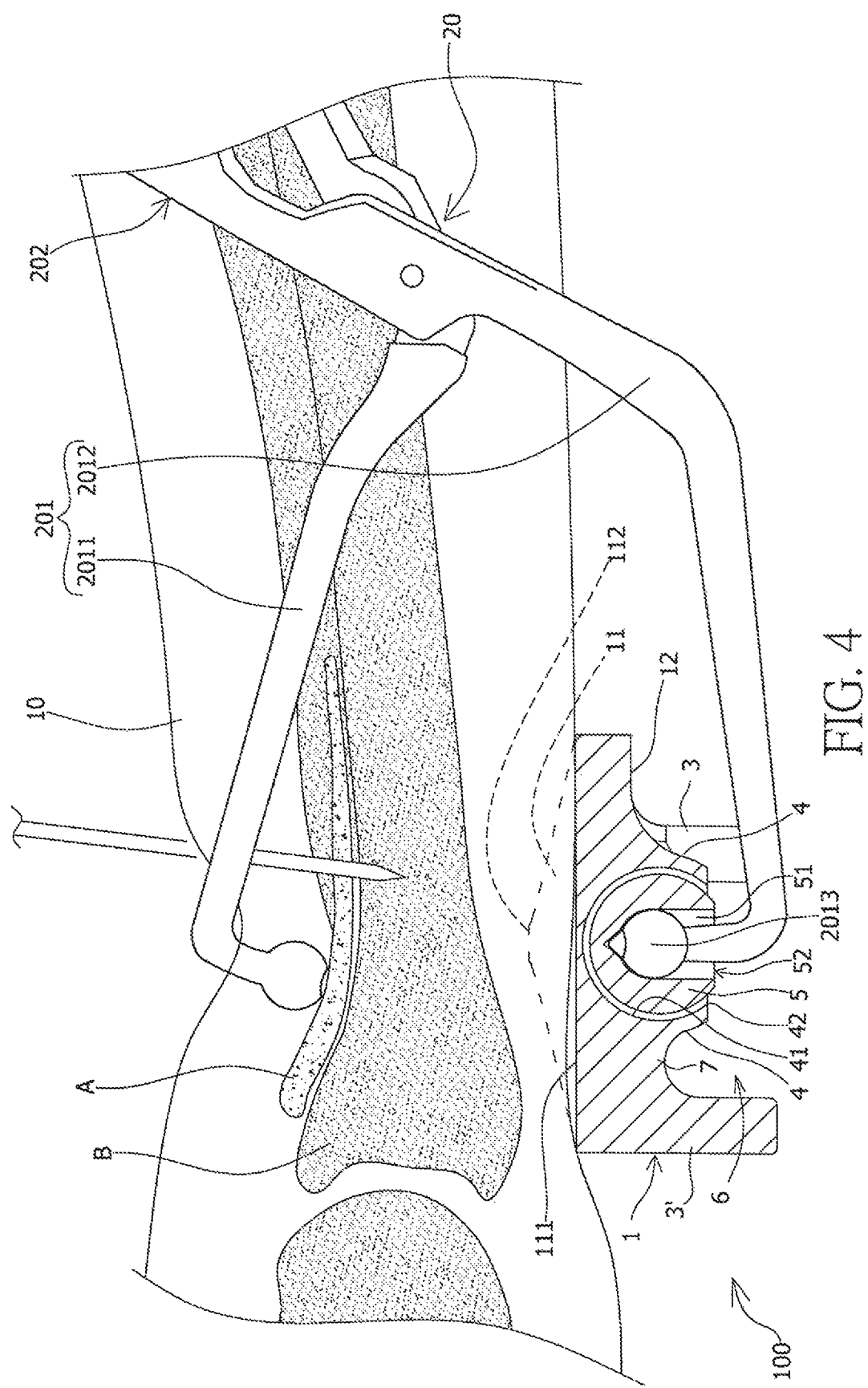
FIG. 4 is a schematic diagram of the first implementation pattern of the present invention used with reduction forceps.

Referring to FIG. 4, the medical assistive device 100 of the present invention is used together with surgical reduction forceps 20, so as to fix the patient's fracture end of radius for the doctor to perform the reduction operation for the fracture of radius. The disclosed reduction forceps 20 is one of the tools for medical operation for fracture. Its structure generally comprises a forceps body 201 for vertical clamping at the front end and a grip part 202 for the doctor to grip at the back end. Wherein the forceps body 201 is divided into an upper forceps body 2011 and a lower forceps body 2012. A spherical part 2013 is located at the end of the upper and lower forceps bodies 2011, 2012.

As shown in FIG. 4, in terms of the combination of medical assistive device 100 of the present invention and surgical reduction forceps 20, the lower forceps body 2012 of reduction forceps 20 is put through the passage 6, and then the spherical part 2013 at the end of lower forceps body 2012 is led in the second slot opening 52 of universal joint 5 and embedded in the embedding slot 51, so that the universal joint 5 is combined with the spherical part 2013, at this point, the universal joint 5 can flexibly rotate against the base 1, and the required angle can be adjusted. Afterwards, the upper forceps body 2011 is combined with a bone plate A, and then the patient's wrist region 10 is placed on the top surface 11 of the base 1, the upper forceps body 2011 combined with the bone plate A is inserted in the surgical incision at the patient's fracture end of radius, with the medical assistive device 100, the patient's bone B can be clamped down, so that the doctor can hold the bone plate A in desired position to perform the reduction operation for the fracture of radius, the operation process is easier, the operating time is shortened, and the efficiency is increased.

The top surface 11 of the base 1 is a cambered surface, closely fitting the lower part of the patient's wrist region 10. The upwarping parts 112, 112' on the right and left sides of base 1 are located on both sides of the patient's wrist region 10, stably keeping the wrist region 10 on the top surface 11 of base, so that the reduction forceps 20 is steadier and unlikely to slip during clamping, the operation stability is enhanced greatly. Secondly, the interconnected passages 6 under the below enable the lower forceps body 2012 of the reduction forceps 20 to reach the lower part of the socket holder 4 through the passages 6 at any angle, so that the spherical part 2013 and universal joint 5 can be combined rapidly. Thus, the time is saved, the efficiency is increased.

Figure 5:
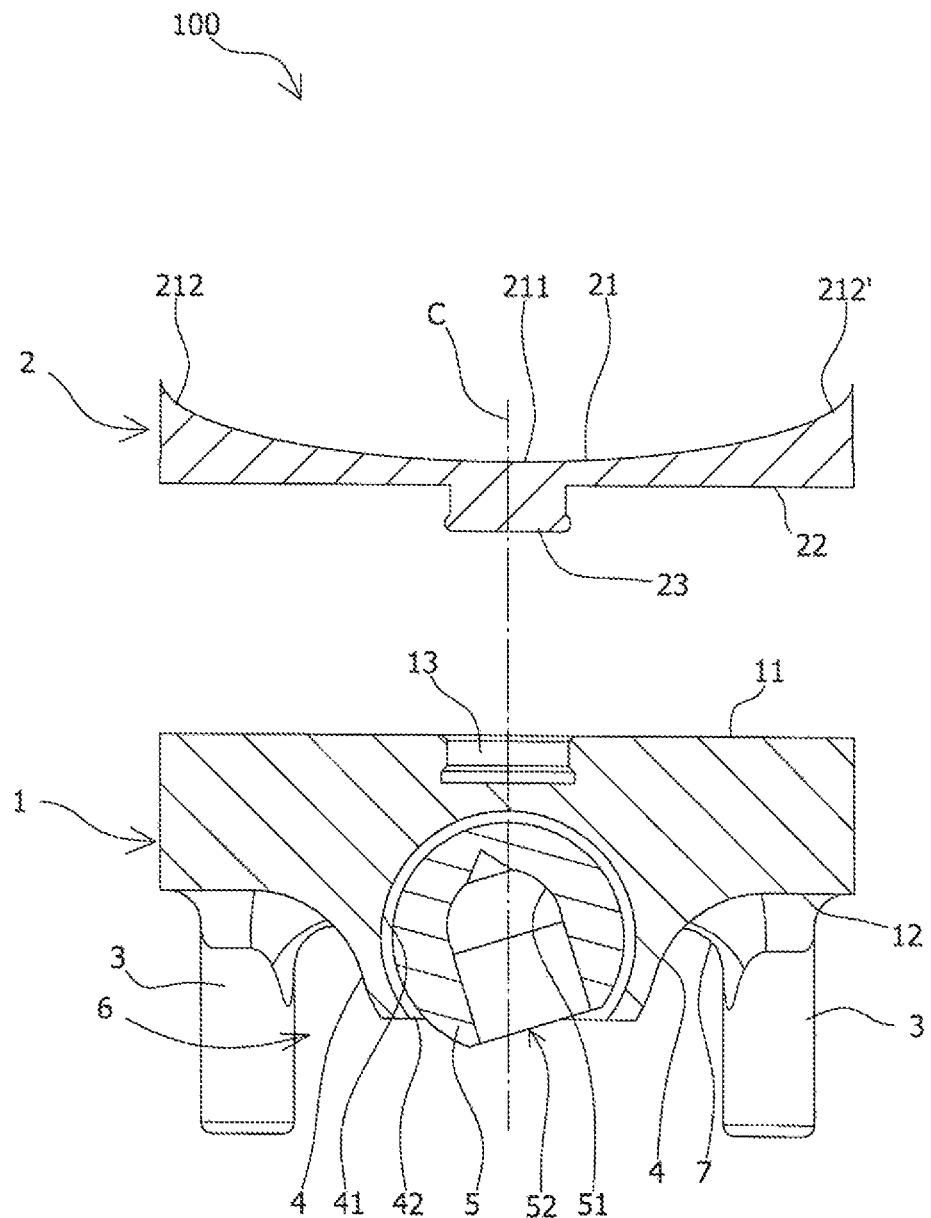
FIG. 5 is an exploded view of the second implementation pattern of the present invention.
Figure 6:
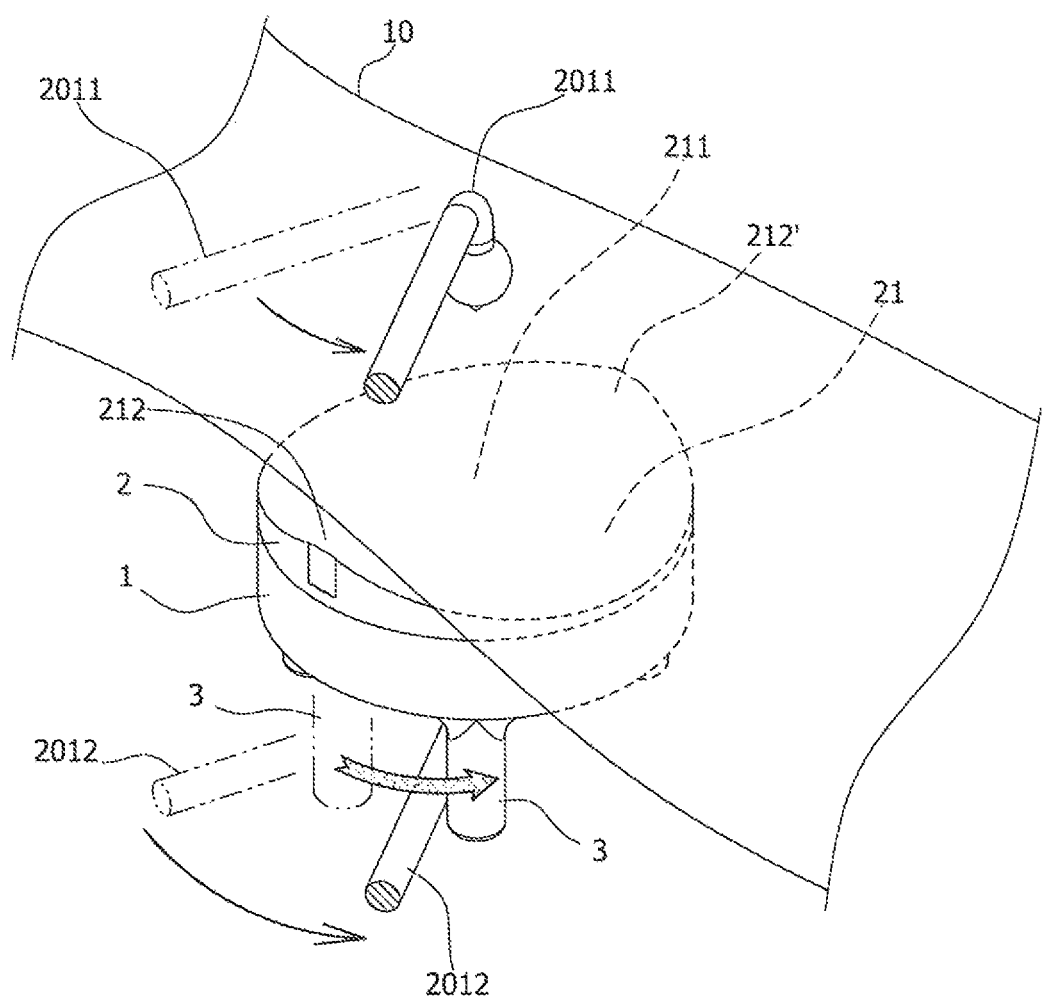
FIG. 6 is a schematic diagram of the second implementation pattern of the present invention used with reduction forceps.

FIGS. 5 and 6 disclose the second implementation pattern of the present invention. The disclosed base 1 structure is still the same as the first implementation pattern, but there is an additional carrier part 2 for placing the patient's wrist region. The carrier part 2 is located on the base 1, one side thereof is the top surface 21, the opposite side is the bottom surface 22 opposite to the top surface 21. Wherein the top surface 21 is the surface contacting the patient's wrist region. In addition, there is a convex shaft 23 in the center of bottom surface 22 of the carrier part 2. There is a pivot hole 13 for the convex shaft 23 in the center of top surface 11 of the base 1. The convex shaft 23 takes the pivot hole 13 as axis, so that the base 1 can rotate 360° horizontally under the carrier part 2.

In the operation, the lower forceps body 2012 of reduction forceps 20 pushes the support columns 3, and then the base 1 rotates 360° round the normal axis C as center, thus, in the reduction operation for the fracture of radius, the doctor can perform 360° rotation operation according to operation requirement at any time, the operation process is easier.

Figure 7:
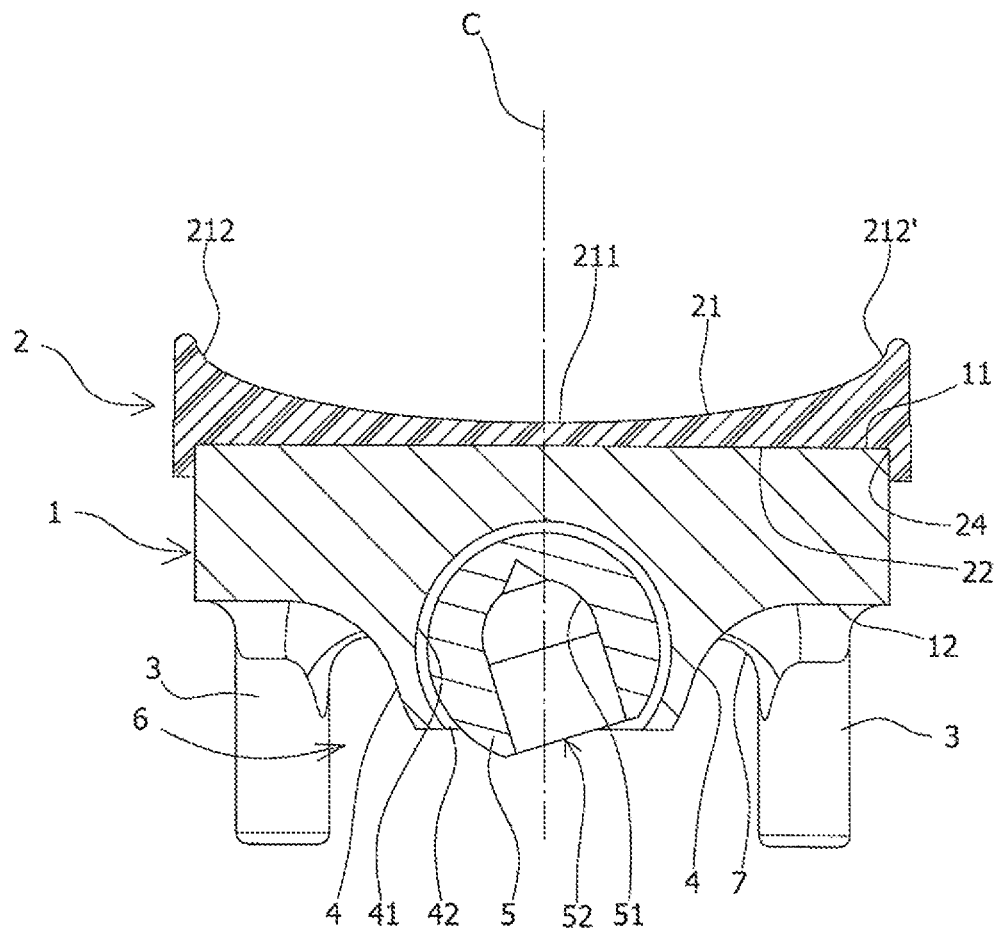
FIG. 7 is a schematic section of the third implementation pattern of the present invention.

FIG. 7 discloses the third implementation pattern of the present invention, the disclosed base 1 structure is still identical with the first implementation pattern, but there is an additional carrier part 2 for placing the patient's wrist region. The carrier part 2 is a soft plastomer, e.g. thermoplastic rubber, silica gel and so on. The bottom surface 22 of the carrier part 2 has a concave shallow slot 24 fitted over the upper part of base 1. The shallow slot 24 enables the carrier part 2 to rapidly cover the base 1 or to be disengaged immediately as required at any time. As it is a soft material, there are soft, friendly and buffering effects on the patient's wrist region.

Figure 8:
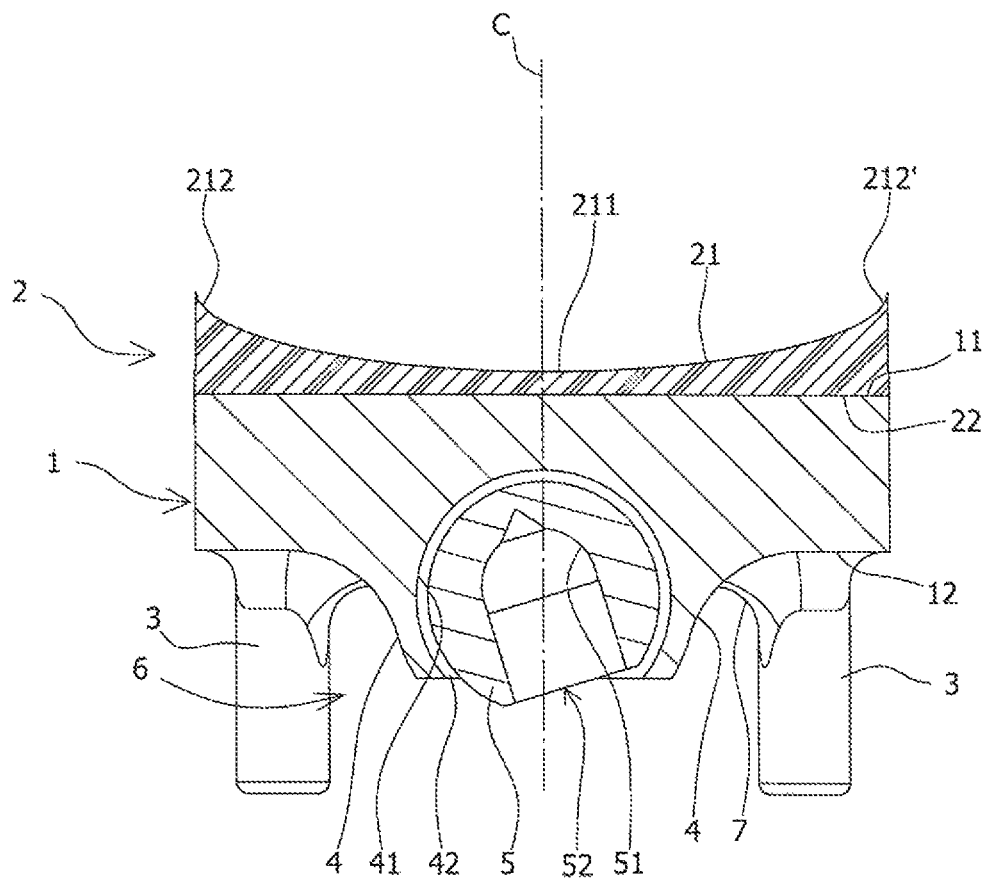
FIG. 8 is a schematic section of the fourth implementation pattern of the present invention.
Figure 9:
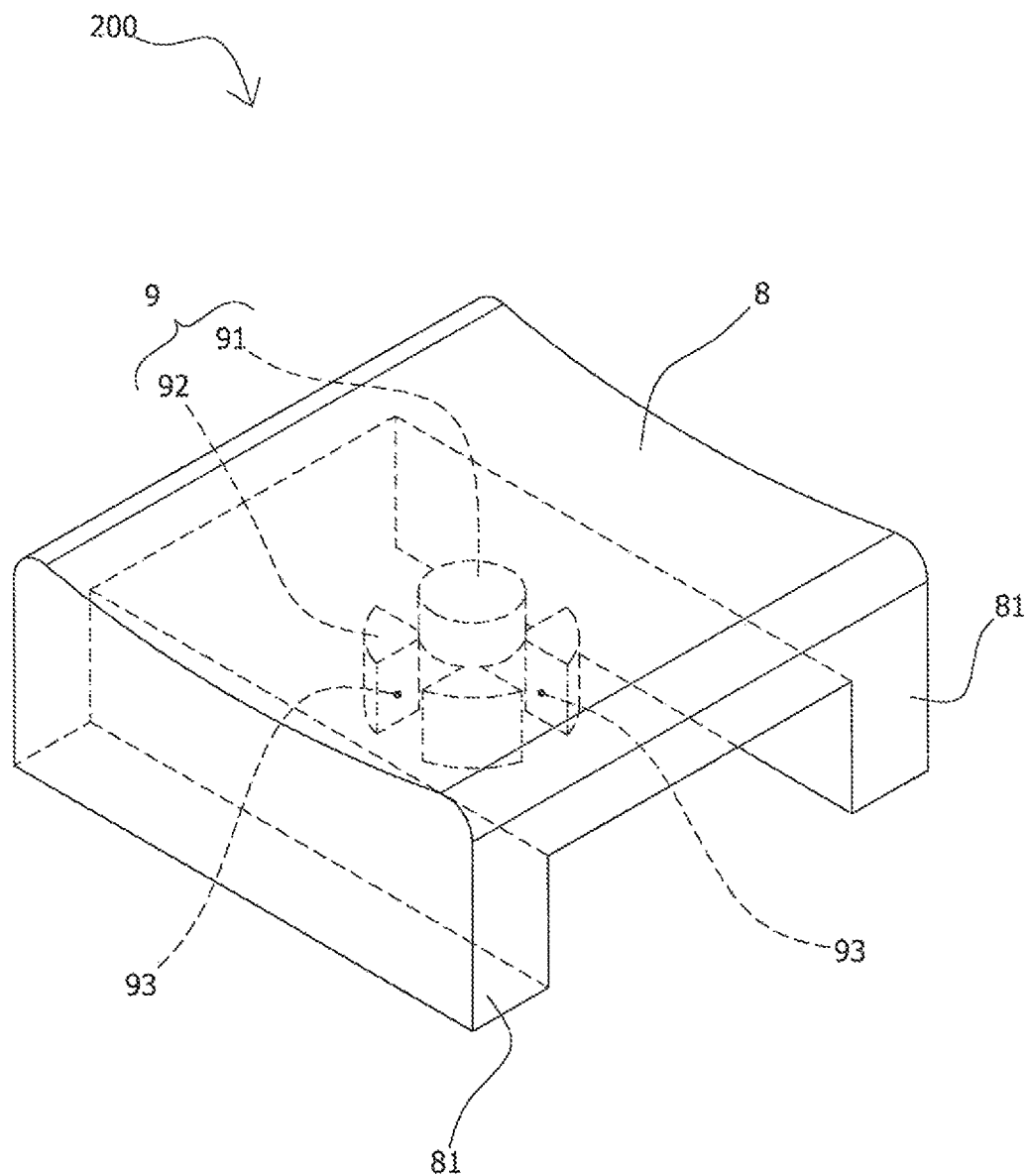
FIG. 9 is a stereogram in top view of reduction forceps aid of previous project.
Figure 10:
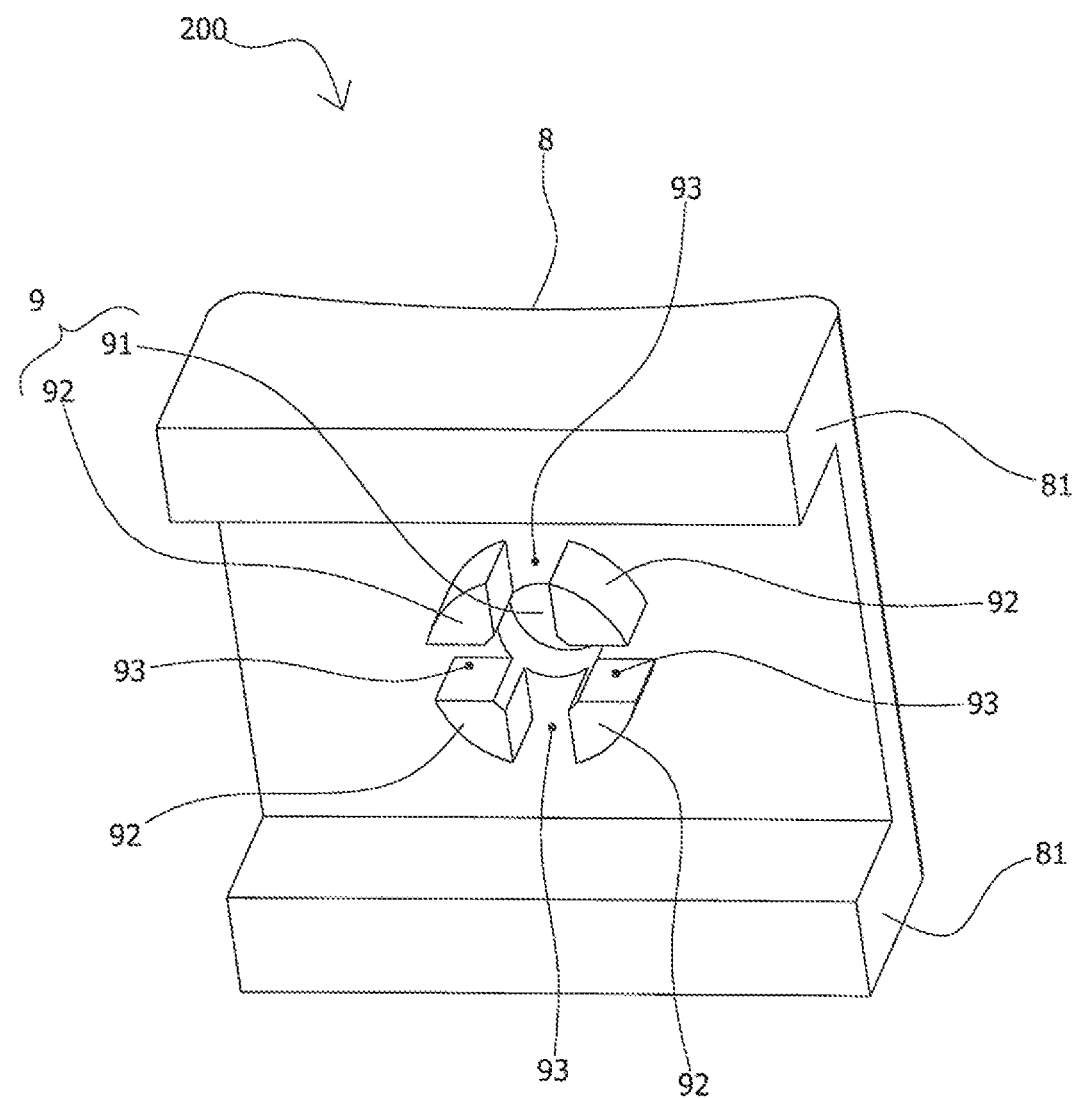
FIG. 10 is a stereogram in upward view of reduction forceps aid of previous project.
Figure 11:
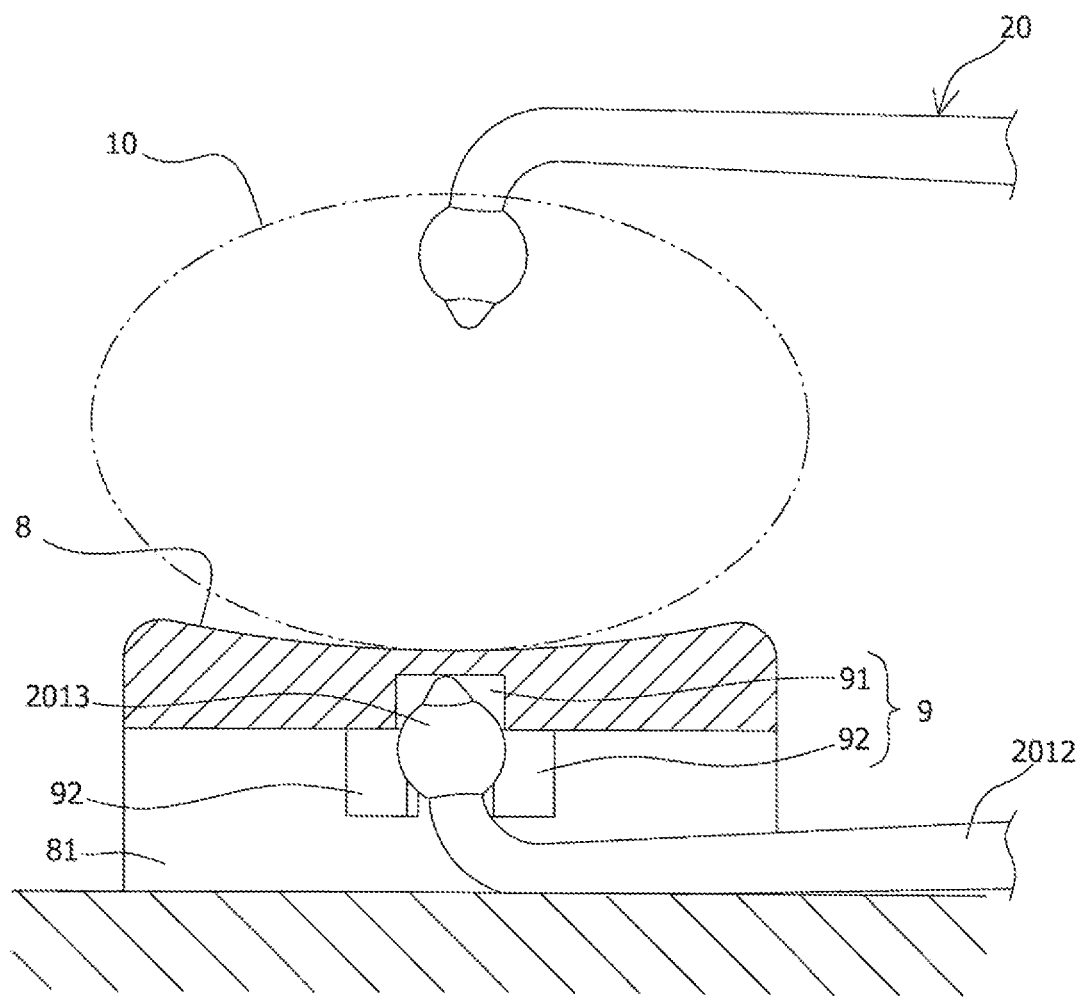
FIG. 11 is a sectional view of reduction forceps aid of previous project.
Figure 12:
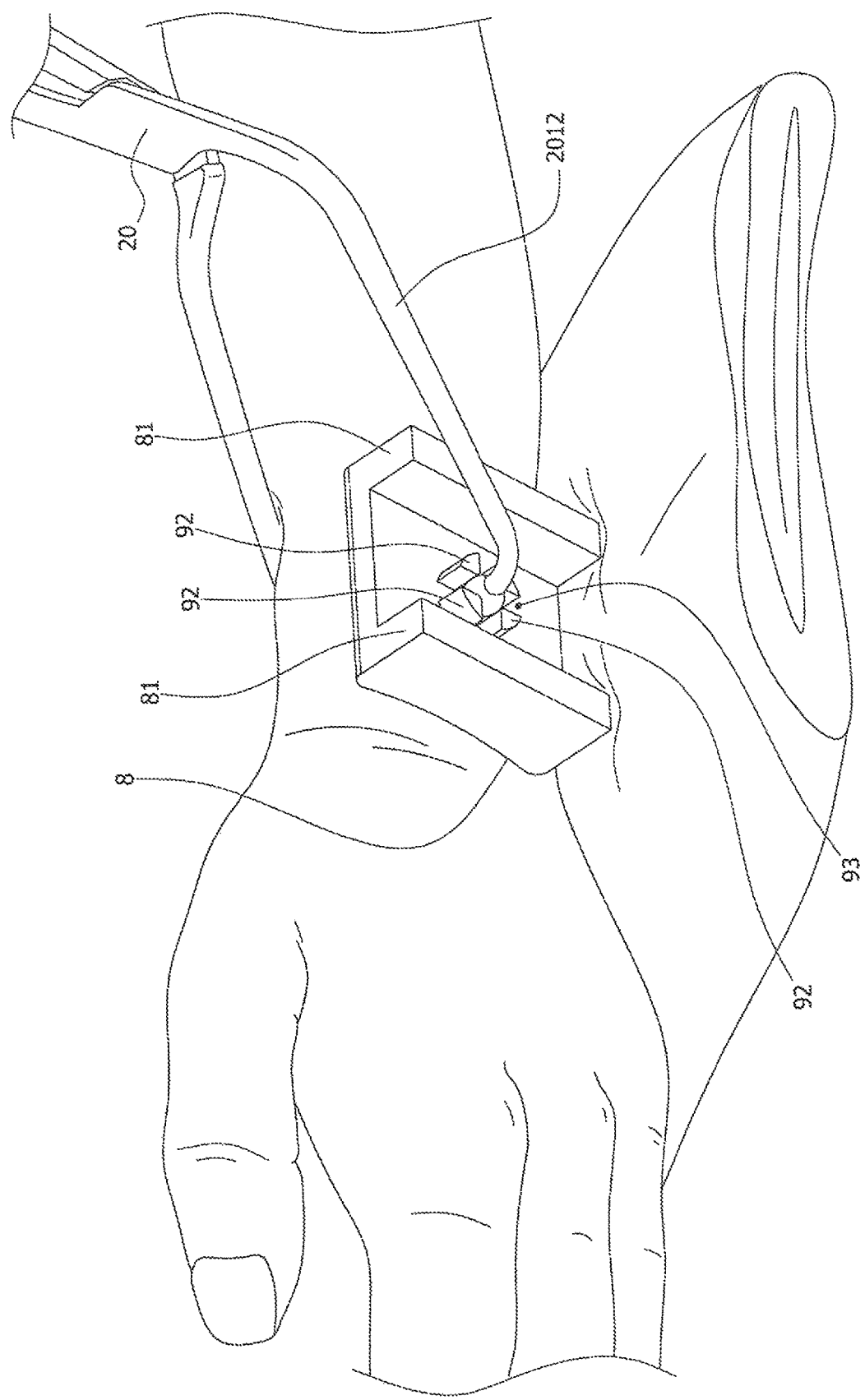
FIG. 12 is a schematic diagram of implementation of reduction forceps aid of previous project.

FIG. 8 discloses the fourth implementation pattern of the present invention, the disclosed base 1 structure is still identical with the implementation patterns, but there is an additional carrier part 2 for placing the patient's wrist region. The carrier part 2 is a soft plastomer. The bottom surface 22 can cover and adhere to the top surface 11 of base 1, but the carrier part 2 is permanently fixed to the base 1. As it is a soft material, there are soft, friendly and buffering effects on the patient's wrist region.

The top surface 21 of the carrier part 2 can be designed as follows, the concave part 211 is located in the center, the upwarping parts 212, 212' are located on the right and left sides, the concave part 211 to the left and right upwarping parts 212, 212' rise at a bend angle, so that the top surface 21 becomes a cambered surface, the patient's wrist region 10 can be stably kept in the center of the top surface 11 of base, the stability is good.

We claim:
1. A medical assistive device for quick positioning of reduction forceps, comprising:
   a base (1), configured for the patient's wrist region, wherein one side of the base (1) is a top surface (11), and the opposite side is a bottom surface (12), the top surface (11) can be used as a surface configured for contacting the patient's wrist region;
   a socket holder (4), which is located under the bottom surface (12) of the base (1), is perpendicular to the bottom surface (12) and protrudes outward toward a vertical axis (C); wherein the socket holder (4) has a round cavity-like hole slot (41), and the hole slot (41) has a first slot opening (42) opened outwards, the first slot opening (42) is located at an end of the socket holder (4) and is also on the same vertical axis (C) as the socket holder (4);

a plurality of support columns (3), which are vertically located on the bottom surface (12) of the base (1) and surround the socket holder (4), and are longer than the socket holder (4); the support columns (3) have passages (6) for a lower forceps body (2012) of a forceps body (201) of reduction forceps (20) to pass through between each other, and the passages (6) are connected to each other;

a universal joint (5), which is a spherical body, is embedded in the hole slot (41) of the socket holder (4), and can be flexibly rotated in the hole slot (41); wherein the universal joint (5) has an embedding slot (51), and the embedding slot (51) has an open second slot opening (52), a hole of the second slot opening (52) is smaller than that of the first slot opening (42) of the socket holder (4); the second slot opening (52) and the first slot opening (42) fit each other, so that a sphere (2013) at an end of the lower forceps body (2012) of the reduction forceps (20) passes through the second slot opening (52) and then be inserted into the embedding slot (51) to be combined.

2. The medical assistive device for quick positioning of reduction forceps defined in claim 1, wherein a center of the top surface (11) is a concave part (111), and right and left sides of the top surface (11) are upwarping parts (112), (112'), the concave part (111) to the right and left upwarping parts (112), (112') rise at a bend angle, so that the top surface (11) becomes a cambered surface.

3. The medical assistive device for quick positioning of reduction forceps defined in claim 2, wherein the support columns (3) are distributed at three equal angles, one of which is located just under the bottom surface (12) of one side end of the concave part (111) of the top surface (11), and can be used at a central support column (3'), the three support columns (3) can form three interconnected passages (6).

4. The medical assistive device for quick positioning of reduction forceps defined in claim 1, wherein the socket holder (4) is a conical convex base protruding from a lower part of the bottom surface (12) of the base and converging outwards; the socket holder (4) and support columns (3) are connected by reinforcing ribs (7); the base (1), support columns (3), socket holder (4) and reinforcing ribs (7) are formed in one.

5. The medical assistive device for quick positioning of reduction forceps defined in claim 1, wherein the shape of the base (1) is one of the following: circular, elliptical, and polygonal.

6. The medical assistive device for quick positioning of reduction forceps defined in claim 1, wherein the top surface (11) of the base (1) is provided with an additional carrier part (2) configured for the patient's wrist region; one side of the carrier part (2) is a top portion (21), and the opposite side is a bottom portion (22), wherein the top portion (21) is a surface configured for contacting the patient's wrist region.

7. The medical assistive device for quick positioning of reduction forceps defined in claim 6, wherein the carrier part (2) has a convex shaft (23) in a center of the bottom portion (22); the center of the top surface (11) of the base (1) has a pivot hole (13) for the convex shaft (23) to be pivoted into and combined; the convex shaft (23) takes the pivot hole (13) as the axis, so that the carrier part (2) can rotate 360° on the base (1).

8. The medical assistive device for quick positioning of reduction forceps defined in claim 6, wherein the carrier part (2) is a soft plastomer; the bottom portion (22) of the carrier part (2) has a concave shallow slot (24) fitted over an upper part of the base (1), so that the carrier part (2) can be combined with or disengaged from the base (1) at any time.

9. The medical assistive device for quick positioning of reduction forceps defined in claim 6, wherein the carrier part (2) is a soft plastomer, the bottom portion (22) of the carrier part (2) can cover and adhere to the top surface (11) of base (1).

10. The medical assistive device for quick positioning of reduction forceps defined in claim 6, wherein a center of the top portion (21) of the carrier part is a recess portion (211), and right and left sides of the top portion (21) are raised portions (212), (212'), the recess portion (211) to the right and left raised portions (212), (212') rise at a bend angle, so that the top portion (21) becomes a cambered surface.

* * * * *